United States Patent [19]

Brindöpke

[11] Patent Number: 4,835,289

[45] Date of Patent: May 30, 1989

[54] PROCESS FOR THE PREPARATION OF 2-OXO-1,3-DIOXOLANES

[75] Inventor: Gerhard Brindöpke, Frankfurt, Fed. Rep. of Germany

[73] Assignee: Hoechst AG, Fed. Rep. of Germany

[21] Appl. No.: 1,349

[22] Filed: Jan. 8, 1987

[30] Foreign Application Priority Data

Jan. 11, 1986 [DE] Fed. Rep. of Germany ....... 3600602

[51] Int. Cl.$^4$ ................... C07D 317/08; C07D 407/00
[52] U.S. Cl. ..................................... 549/229; 549/230
[58] Field of Search ............................... 549/229, 230

[56] References Cited

PUBLICATIONS

English translation of published Japanese patent application No. 55-103592.

G. Rokicki et al., Monatshefte fur Chemie, vol. 115 (1984), pp. 205–214.

G. Rokicki, Makromol. Chem., vol. 186 (1985), pp. 331–337.

L. Toke et al., Acta Chimica Academiae Scientiarum Hungaricae, vol. 101(1-2) (1979), pp. 47–51.

English translation of Russian Patent No. SU 1,126,569 (11-30-84).

*Primary Examiner*—Richard L. Raymond
*Assistant Examiner*—Raymond Covington
*Attorney, Agent, or Firm*—Bierman and Muserlian

[57] ABSTRACT

A process for the preparation of 2-oxo-1,3-dioxolanes by reaction of epoxides with carbon dioxide in the presence of alkali iodides wherein at least one epoxy compound is reacted in the presence or absence of inert solvent either with a combination of A) at least one alkali iodide and B) at least one compound of the group a) polyol and b) an ether or polyether or, if the epoxy compound already has the structural features of the compounds Ba) and Bb), with the alkali iodide A) alone, at temperatures from 40° to 180° C. while introducing carbon dioxide at normal pressure or at slightly increased pressure, to form the corresponding organic carbonates. The 2-oxo-1,3-dioxolanes obtained are used for the preparation of synthetic resins, containing urethane groups, in the form of coatings of molded bodies.

15 Claims, 1 Drawing Sheet

PROCESS FOR THE PREPARATION OF 2-OXO-1,3-DIOXOLANES

It is known that 2-oxo-1,3-dioxolanes (also termed alkylene carbonates) can be obtained by reacting alkylene oxides with carbon dioxide in the presence of catalysts. In German Offenlegungsschrift No. 2,611,087 a process is described for the preparation of alkylene carbonates of the general formula

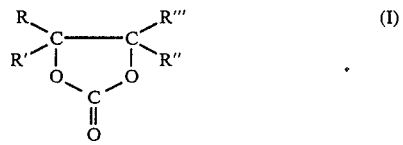

an alkylene oxide being reacted with $CO_2$ at temperatures between 0° and 200° C. and a pressure of 1 to 98 bar in the presence of a catalyst which consists of a combination of a protic substance of the formula ROH and a nitrogen-containing base. Protic substances are water, alcohols and phenol. Trimethylamine, triethylamine, pyridine or dimethylaniline are quoted as nitrogen-containing bases. With respect to the substituents R to R''' it is only stated generally that these may be hydrogen or an alkyl, aryl, cycloalkyl or aralkyl radical. More detailed information is not given. In the examples only ethylene oxide and propylene oxide are quoted as alkylene oxides and all the work is carried out under pressure (10 bar minimum).

In "Monatshefte fur Chemie" 115 (1984), 205–214, G. Rokicki and co-workers describe the preparation of cyclic carbonates from $CO_2$ and oxiranes in the presence of alkali-metal salt phase transfer catalysts. Crown ethers, 1,4-diazabicyclo[2,2,2]-octane (sic) (DABCO), N,N,N,N-tetramethylethylene diamine (TMEDA) and triethylbenzylammonium chloride (TEBA), but also (with reduced yield) polyethylene glycol are used as phase transfer agents. High yields, i.e. almost theoretical values, are achieved only by means of initial pressures of 40 bar. If 6 bar is employed, a yield which is lower by approximately 25% is obtained and at 1 bar only 8% is actually obtained. Alkali-metal salts used are alkali halides and carbonates. Ethylene oxide and propylene oxide, epihalohydrines, glycidol, N-butyl (sic), allyl and phenyl glycidol ethers, styrene oxide and 3,3-disubstituted cyclohexene oxide are quoted as epoxy components.

A further paper by G. Rokicki (Makromol. Chem. 186, 331–337 (1985)) describes the preparation of cyclic dicarbonates by the use of 2,2-bis[4-(2,3-epoxypropoxy)phenyl]-propane or an epoxy resin (® Epikote 828) under the conditions specified above.

The preparation of alkylene carbonates by treatment of alkylene oxides with $CO_2$ in the presence of an alcohol such as methanol and an (un)substituted phosphine compound as catalyst is additionally known (PCT WO 84/03, 701). Increased pressure (21 bar) is also employed in this case. In addition, it emerges from the publication that the presence of both the alcohol and also of the phosphine is absolutely essential to obtain a good yield.

It therefore emerges from the prior art that to achieve a high yield high pressures must always be employed, and/or that the presence of a protic substance is necessary to achieve satisfactory yields.

The disadvantages mentioned can be avoided according to the present invention.

The subject of the invention is therefore a process for the preparation of 2-oxo-1,3-dioxolanes by reaction of epoxides with carbon dioxide in the presence of alkali iodides, wherein at least one epoxy compound is reacted in the presence or absence of an inert solvent with either a combination of (A) at least one alkali iodide and (B) at least one compound of the group (a) polyol and (b) an ether or polyether having the structures

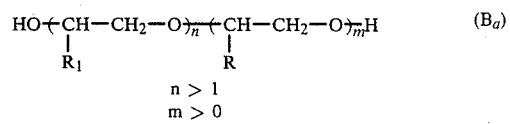

and

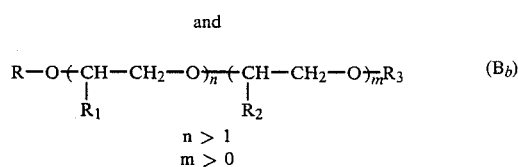

in which
R is identical or different and is alkyl, aralkyl containing 1–10 C atoms in the alkyl group in each case, or aryl,
$R_1$, $R_2$ are identical or different and are hydrogen or alkyl containing 1–10 C atoms and
$R_3$ is identical to R, but may also be hydrogen,
or, if the epoxy compound already has the structural features of the compounds (Ba) and (Bb), with the alkali iodide (A) alone, at temperatures from 40° to 180° C. while introducing carbon dioxide at normal pressure or at a slightly increased pressure to form the corresponding organic carbonates. The epoxy groups in the starting compounds can be reacted partially or completely by this process.

The advantage of the process is the application of normal or slightly increased pressure, no large equipment expenditure being necessary. Furthermore, the high selectivity of the reaction should be emphasized, i.e. virtually no epoxy side-reactions such as homopolymerization occur which have been described for this reaction mechanism in the state of the art. Furthermore, it is possible to produce storage-stable epoxy/carbonate mixtures by the process which have a multifunctionality and are available for many fields of application. Furthermore the neutrality of the catalyst used does not lead to any inhibition of possible consequent reactions at the epoxy group or at the carbonate group, for example in the case of an etherification or esterification reaction of the epoxide group catalysed by an acid.

The pressure to be used in the process is in general 1 to 10, preferably 1 to 5 and in particular 1 to 3 bar. In most cases normal pressure is applied, but if necessary, increased pressure can also be employed in the process. The preferred temperature range of the process is 60 to 180, in particular 80° to 150° C.

The following compounds are, for example, suitable as epoxy components which can be reacted with $CO_2$ and which in general have at least one terminal epoxy group: aliphatic epoxides containing at least 6 C atoms such as hexene, octene, and dodecene 1-oxides, glycidol and epihalohydrines of the formula

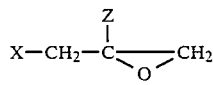 (2)

in which Z represents a hydrogen atom, a methyl or ethyl group and X represents a halogen atom or an OH group. Examples of such epihalohydrines are epichlorohydrine, epibromohydrine, 1,2-epoxy-2-methyl-3-chloropropane and 1,2-epoxy-2-ethyl-3-chloropropane.

Further epoxy components which may be used according to the invention include, for example, epoxy components which contain on average at least one terminal 1,2-epoxy group. Preferably these are epoxy compounds which contain on average at least one substituted or unsubstituted glycidyl ether group or a substituted or unsubstituted glycidyl ester group, furthermore, epoxydized, multiply unsaturated compounds and epoxides containing amide or urethane groups.

Epoxy compounds which contain on average at least one substituted or unsubstituted glycidyl ether group which has the formula

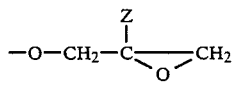 (3)

in which Z represents hydrogen, a methyl or an ethyl group, are, for example, glycidyl or polyglycidyl ethers of mono- or polyhydric alcohols, phenol or polyhydric phenols which have one or more aromatic nuclei and also of novolacs, polyglycidyl ethers of alcoholic polyhydroxyl compounds obtained by an addition reaction of polyhydric phenols containing one or more aromatic nuclei with alkylene oxides which have 2 to 4 C atoms, and polyglycidyl ethers of alcoholic polyhydroxyl compounds which have one or more alicyclic rings. Phenol, the various cresols, resorcin, hydroquinone, pyrogallol, phloroglycine (sic), 1,5-, 2,7-, 2,6-dihydroxynaphthalenes and the like, 2,2-bis(p-hydroxyphenyl)propane and 2,2-bis(p-hydroxyphenyl)methane (known as bisphenol A or F respectively), 2,4'-dihydroxydiphenylmethane and the like are, for example, used as phenols. Polyhydric alcohols which can be reacted to form glycidyl ethers are, for example, ethylene glycol, propylene glycol, butyl glycol, neopentyl glycol, hexylene glycol, polyethylene glycol, polypropylene glycol and the like. Suitable monohydric alcohols are for example ethanol, n-butanol and ethylhexanol. Among these are included also plasticized epoxy resins with terminal epoxy groups which are prepared by partial reaction of the epoxy groups of epoxy resins containing at least two epoxy groups with substances containing OH and COOH such as polyhydric alcohols, for example the abovementioned diols, polycarboxylic acids or polyesters containing carboxyl or OH groups.

Further epoxy compounds are glycidyl esters of saturated or ethylenically unsaturated carboxylic acids containing at least one substituted or unsubstituted glycidyl ester group of the following formula

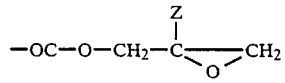 (4)

in which Z represents a hydrogen atom, a methyl or an ethyl group. The acids are aliphatic or aromatic, saturated or unsaturated mono- or polycarboxylic acids, for example acrylic acid, methacrylic acid, adipic acid, the various phthalic acids, tetrahydro- and hexahydrophthalic acid and the like. A very common glycidyl ester is available commercially and is the glycidyl ester of a mixture of saturated monocarboxylic acids with a chain length of 9 to 11 carbon atoms consisting mainly (approximately 94%) of tertiary acids (glycidyl ester of Versatic acid). Included here are also epoxy resins which have been obtained by copolymerization of glycidyl methacrylate with other copolymerizable monomers such as styrene and (meth)acrylic acid esters.

Furthermore, epoxides containing amide or urethane groups are suitable for the reaction, for example triglycidyl isocyanurate or glycidol-masked hexamethylene diisocyanate. Mixtures of the said compounds may also be used.

In the combination which catalytically influences the reaction of the epoxides with $CO_2$ the component (A) is at least one alkali iodide such as potassium, sodium or lithium iodide. Compounds (B) have the general structures

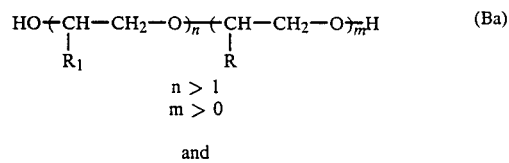 (Ba)

and

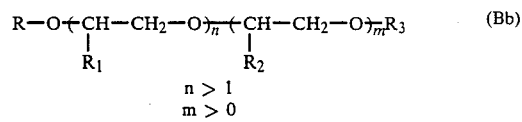 (Bb)

in which
R is identical or different and is alkyl, aralkyl containing 1–10 C atoms in the alkyl group in each case, or aryl,
$R_1$, $R_2$ are identical or different and are hydrogen or alkyl containing 1–10 C atoms and
$R_3$ is identical to R, but may also be hydrogen.

In (Ba) n is preferably 2 to 40, especially 2 to 20, and m is preferably 0 to 40, especially 0 to 20. n+m stands preferably for 2 to 40. In (Bb) n is preferably 1 to 40, especially 1 to 20, and m is preferably 0 to 40, especially 0 to 20. n+m stands here preferably for 1 to 40.

Examples of compounds (Ba) are, for example, polyethylene glycols and polypropylene glycols such as diethylene glycol, triethylene glycol, tetraethylene glycol and dipropylene glycol.

Examples of compounds (Bb) are, for example, ethers or polyethers such as ethylene glycol monomethyl and monobutyl ether, dimethoxyethane, diethylene glycol monomethyl ether and diethylglycolmonobutyl ether, diethylene glycol dimethyl ether and diethylene glycol diethyl ether, triethylene glycol monoethyl ether and triethylene glycol dimethylether, propylene glycol monobutyl ether and also a monobutyl ether of a polyglycol for the preparation of which a mixture of ethylene oxide and propylene oxide is used.

The compounds (Ba) and (Bb) are in each case used in quantities of 1–95, preferably 1–50, in particular 10–30% by weight referred to the epoxy component.

If the epoxides to be reacted have themselves the structural features quoted for the compounds (Ba) and (Bb), the use of a compound of the type (Ba) or (Bb) may be dispensed with.

Examples of such epoxides are glycidyl ethers of di-, tri- or polyethylene or propyleneglycols, diglycidyl ether of diethylene glycol, polypropylene or polyethylene glycol. On the other hand said epoxides, since they have the necessary structural features, can assume in this process the tasks of the compounds (Ba) and (Bb) in the carbonating of epoxides which contain no polyether groups. In this case mixtures containing the abovementioned epoxy compounds may, for example, be present in the process according to the invention.

The alkali iodides (A) are in general used individually or mixed in quantities of 0.01 to 1, preferably 0.05 to 1 and in particular 0.05 to 0.5% by weight referred to the weight of the epoxy component.

The reaction time may vary within wide limits. In general the reaction is carried out in a manner such that the epoxy groups are virtually completely reacted. The reaction is followed, for example, by titration of the epoxy groups and is terminated at the point which, within the framework of analytical accuracy, is regarded as "low in epoxy groups or epoxy-free". In this manner alkyl carbonates are obtained from any epoxy compounds which can be processed further in a known manner.

In addition, if polyepoxides are present, the reaction can be terminated at any desired point so that compounds are obtained which, in addition to carbonate groups, also have epoxy groups which are still intact. The latter has the advantage that, depending on the nature of the desired further processing and the application of the products, a selective reaction of the epoxy group next to the carbonate group (and vice versa) can take place. In general, in the case of polyepoxides (number of epoxy groups $n \geqq 2$) the reaction will be carried out in this case in a manner such that the proportion of reacted epoxy groups is 0.1–0.9 n.

The reaction of the epoxy compounds with $CO_2$ may take place in the presence or absence of solvents. In general no solvents are used if the epoxy compounds exist in the liquid state above 50° C. However, if they are viscous melts at the reaction temperature and as a result make a homogeneous dispersion of the carbon dioxide difficult on stirring or if a further processing of the reaction product in solution is envisaged, solvents are in general used.

Aromatic hydrocarbons such as toluene, xylene and hydrocarbon mixtures produced in petroleum cracking, dioxane, tetrahydrofuran, and other solvents which are inert towards epoxy groups can be used as solvents.

The products obtained by the process according to the invention are used for the preparation of synthetic resins, containing urethane groups, in the form of coatings or molded bodies.

In the following examples P always denotes parts by weight and % always denotes % by weight.

EXAMPLES

General specification for the preparation of carbonates from epoxides

The epoxide with the epoxide content quoted in the table was introduced into an apparatus (if necessary, pressurized apparatus) equipped with a stirrer, thermometer and a gas inlet tube and, after addition of the catalyst (A) and the component (B) heated to the specified reaction temperature while vigorously stirring and while introducing carbon dioxide. If necessary, the reaction apparatus was flushed out beforehand with carbon dioxide.

With carbon dioxide being continuously introduced, stirring was continued at a normal pressure of 1 bar at the specified reaction temperature until the residual epoxy content, which was determined by titration, was as required. Hot filtration was then carried out if turbidity was present. The yield refers to the conversion which is determined by the residual epoxy content.

The meanings in the table are as follows:

| | |
|---|---|
| ® Beckopox EP 140 | technical diglycidyl ether of bisphenol A (trade designation of HOECHST AG) |
| ® Epicote 1001 | technical diglycidyl ether of bisphenol A (trade designation of DOW, USA) |
| ® Denacol | |
| EX 861 | Polyethylene glycol diglycidyl ether |
| EX 830 | |
| EX 920 | Polypropylene glycol diglycidyl ether (trade designation of Nagase, Japan) |
| ® Cardura E 10 | Glycidyl ester of Versatic acid (Shell commercial product) |
| Beckopox 080 | Glycidyl ether of ethylhexanole (trade designation of HOECHST AG) |
| Butyl glycol | Ethylene glycol monobutyl ether |
| DMDG | Diglycol dimethyl ether |
| DMTG | Triglycol dimethyl ether |
| TEG | Triethylene glycol |
| B11/50 | Polyglycol B11/50 (based on ethylene propylene oxide) (designation of HOECHST AG) |
| DEGMM | Diethylene glycol monomethyl ether |
| PE 300 | Polyethylene glycol PE 300 (mean molecular mass 300) |

| Ex. | Epoxide | Epoxy content (%) | Quantity (P) | Catalyst | Quantity (P) | % | Ether glycol | Quantity (P) | Temp. (°C.) | Reaction time (h) | Yield % | Epoxy content (%) | $CO_2$ used (%) |
|---|---|---|---|---|---|---|---|---|---|---|---|---|---|
| 1 | Beckopox EP 140 | 8.6 | 511 | KI | 0.77 | 0.15 | DMTG | 270 | 140 | 11 | 98.1 | 0.19 | 18.5 |
| 2 | Beckopox EP 140 | 8.6 | 1002 | KI | 1 | 0.1 | DMDG | 140 | 140 | 12 | 92.4 | 3.09 | 12.0 |
| 3 | Beckopox EP 140 | 8.6 | 513 | NaI | 0.77 | 0.15 | DMTG | 271 | 140 | 14 | 92.8 | 0.18 | 18.3 |
| 4 | Beckopox EP 140 | 8.6 | 565 | KI | 0.85 | 0.15 | 1-methoxy-propanol | 170 | Reflux | 15 | 96.1 | 0.24 | 18.1 |
| 5 | Beckopox EP 140 | 8.6 | 970 | KI | 1.48 | 0.15 | DMDG | 512 | 140 | 17 | 93.7 | 0.25 | 18.1 |
| 6 | Beckopox EP 140 | 8.6 | 924 | KI | 1.39 | 0.15 | Butyl glycol | 488 | 140 | 13 | 92.3 | 0.15 | 18.0 |
| 7 | Beckopox EP 140 | 8.6 | 972 | KI | 1.49 | 0.15 | TEG | 513 | 140 | 11 | 91.6 | 0.18 | 18.2 |
| 8 | Beckopox EP 140 | 8.6 | 919 | KI | 1.40 | 0.15 | B11/50 | 485 | 140 | 9 | 90.2 | 0.2 | 18.0 |
| 9 | Beckopox EP 140 | 8.6 | 928 | KI | 1.42 | 0.15 | DEGMM | 490 | 140 | 10 | 93.2 | 0.1 | 18.5 |
| 10 | Beckopox EP 140 | 8.6 | 517 | KI | 0.78 | 0.15 | PE 300 | 273 | 140 | 10 | 97.9 | 0.2 | 18.4 |
| 11 | Epicote 1001 | 3.33 | 817 | KI | 0.8 | 0.1 | DMTG | 381 | 140 | 10 | 94.2 | 0.1 | 8.0 |
| 12 | Epicote 1001 | 3.33 | 1000 | KI | 1 | 0.1 | DMDG | 262 | 120 | 6 | 95.4 | 1.63 | 4.0 |

-continued

| Ex. | Epoxide | Epoxy content (%) | Quantity (P) | Catalyst | Quantity (P) | % | Ether glycol | Quantity (P) | Temp. (°C.) | Reaction time (h) | Yield % | Epoxy content (%) | $CO_2$ used (%) |
|---|---|---|---|---|---|---|---|---|---|---|---|---|---|
| 13 | Epicote 1001 | 3.33 | 1000 | KI | 1 | 0.1 | DMDG | 468 | 140 | 13 | 96.2 | 0.1 | 7.9 |
| 14 | Denacol EX 861 | 2.42 | 980 | KI | 1 | 0.1 | DMDG | 420 | 130 | 12 | 95.2 | 0.05 | 6.0 |
| 15 | Denacol EX 920 | 9.25 | 989 | KI | 1 | 0.1 | — | — | 120 | 15 | 92.6 | 0.1 | 19.4 |
| 16 | Denacol EX 920 | 9.25 | 1509 | KI | 1.51 | 0.1 | — | — | 120 | 5 | 95.2 | 4.15 | 10.7 |
| 17 | Denacol EX 830 | 6.20 | 992 | KI | 1 | 0.1 | — | — | 140 | 13 | 94.1 | 0.1 | 14.0 |
| 18 | Denacol EX 830 | 6.2 | 1030 | KI | 1.03 | 0.1 | — | — | 120 | 4 | 96.2 | 2.88 | 7.6 |
| 19 | Cardura E 10 | 6.9 | 500 | KI | 0.75 | 0.15 | DEGMM | 214 | 140 | 18 | 95.2 | 0.15 | 14.3 |
| 20 | Dodecen-1-acid | 8.7 | 409 | KI | 0.61 | 0.15 | TEG | 175 | 140 | 14 | 91.6 | 0.21 | 18.4 |
| 21 | Beckopox 080 | 8.5 | 507 | KI | 0.75 | 0.15 | DEGMM | 214 | 140 | 14 | 95.8 | 0.13 | 18.3 |
| 22 | n-butylglycidyl-ether | 12.3 | 432 | KI | 2.7 | 0.5 | — | — | 130 | 15 | 95.9 | 0.25 | 22.1 |
|  | Denacol EX 830 | 6.2 | 108 |  |  |  |  |  |  |  |  |  |  |
| 23 | Beckopox EP 140 | 8.6 | 532 | KI | 3.8 | 0.5 | — | — | 140 | 14 | 95.8 | 0.15 | 17.0 |
|  | Denacol EX 830 | 6.2 | 228 |  |  |  |  |  |  |  |  |  |  |
| 24 | Glycidyl methacrylate | 11.3 | 840 | KI | 4.2 | 0.5 | 1-methoxy-propanol | 360 | 80 | 21 | 94.5 | 0.4 | 22.4 |

I claim:

1. A process for the preparation of 2-oxo-1,3-dioxlolanes by a reaction of epoxides with carbon dioxide in the presence of alkali iodides, wherein at least one epoxy compound is reacted in the presence or absence of an inert solvent with a combination of (A) at least one alkali iodide and (B) at least one compound of the group (a) polyethylene glycol and polypropylene glycol and (b) monoether and polyether of mono- and polyethylene glycol and mono- and polypropylene glycol at temperatures from 40° to 180° C. while introducing carbon dioxide at normal pressure or at slightly increased pressure, to form the corresponding organic carbonates.

2. The process as claimed in claim 1, wherein a pressure of 1 to 10 bar is employed.

3. The process as claimed in claim 1, wherein sodium or potassium iodide is used in quantities of 0.01 to 1% by weight, referred to the epoxy component, is used as alkali iodide.

4. The process as claimed in claim 1, wherein (Ba) or (Bb) are selected from the group consisting of di-, tri- and polyglyol or mono- and diether.

5. The process as claimed in claim 4, wherein (Ba) or (Bb) are selected from the group consisting of diethylene, triethylene, tetraethylene and dipropylene glycol, ethylene glycol monomethyl and monobutyl ether, dimethoxyethane, diethylene glycol monoethyl and monobutylether, diethylene glycol dimethyl and diethyl ether, triethylene glycol monomethyl and dimethyl ether, propylene glycol monobutylether and ethylene propylene glycol monobutylethyl.

6. The process as claimed in claim 1, wherein the compounds (Ba) and (Bb) are used in quantities of 1 to 95, by weight, referred to the epoxy ocmponents.

7. The process as claimed in claim 1, wherein the reaction of the epoxy compound is only partly carried out with carbon dioxide so that compounds are obtained which, in addition to carbonate groups, also have epoxy groups which are still intact.

8. The process as claimed in claim 1, wherein the epoxides are aliphatic epoxides containing at least 6 C atoms and having at least one terminal epoxy group.

9. The process as claimed in claim 1, wherein the epoxides are compounds of the formula (2)

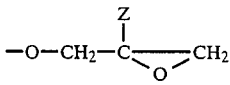

in which $Z=H$, $CH_3$ or $C_2H_5$ and $X=$ halogen or OH.

10. The process as claimed in claim 1, wherein the epoxides contain an average of at least one terminal 1,2-epoxy group from the group consisting of glycidyl ether groups of the formula (3)

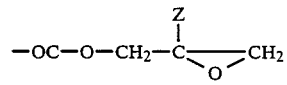

and glycidyl ester groups of the formula (4)

$$-OC-O-CH_2-\underset{\underset{O}{|}}{\overset{\overset{Z}{|}}{C}}\!\!-\!\!CH_2$$

in which formulae Z has the same meaning as in formula (2).

11. The process as claimed in claim 1, wherein the epoxides are members of the group consisting of epoxidized, multiple unsaturated compounds and epoxides containing amide or urethane groups.

12. The process as claimed in claim 1, wherein the epoxides are plasticized epoxy resins with terminal epoxy groups prepared by partial reaction of the epoxy groups of the epoxy resin containing at least two epoxy groups with substances containing at least one member of the group consisting of OH and COOH.

13. A process for the preparation of a 2-oxo-1,3-dioxolane comprising reacting an epoxy compound containing a structure selected from the group consisting of

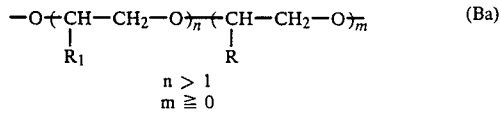

and

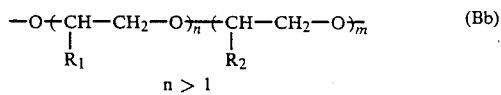

-continued
$m \geq 0$ wherein the R's are individually selected from the group consisting of alkyl of 1 to 10 carbon atoms, aryl and aralkyl having 1 to 10 alkyl carbon atoms, $R_1$ and $R_2$ are individually selected from the group consisting of hydrogen and alkyl of 1 to 10 carbon atoms with an alkali metal iodide at temperatures from 40° to 180° C. while introducing carbon dioxide at normal or slightly increased pressure in the presence or absence of an inert solvent to form the corresponding organic carbonates.

14. The process of claim 1 wherein the pressure is 1 to 3 bar.

15. The process of claim 1 wherein the compounds (Ba) and (Bb) are used in an amount of 10 to 30% by weight based on the epoxy component.

* * * * *